(12) United States Patent
Schmidt et al.

(10) Patent No.: US 8,774,915 B2
(45) Date of Patent: *Jul. 8, 2014

(54) DIVERSE CAPACITOR PACKAGING FOR MAXIMIZING VOLUMETRIC EFFICIENCY FOR MEDICAL DEVICES

(75) Inventors: Craig L. Schmidt, Eagan, MN (US); William L. Johnson, Vadnais Heights, MN (US); Steven Joseph May, Minnetonka, MN (US); Christian S. Nielsen, River Falls, WI (US); John Daniel Norton, Saint Paul, MN (US); Anthony W. Rorvick, Champlin, MN (US); Jeffrey A. Swanson, Cambridge, MN (US); William K. Wenger, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 853 days.

This patent is subject to a terminal disclaimer.

(21) Appl. No.: 12/977,666

(22) Filed: Dec. 23, 2010

(65) Prior Publication Data
US 2011/0160784 A1    Jun. 30, 2011

Related U.S. Application Data

(63) Continuation of application No. 11/622,245, filed on Jan. 11, 2007, now Pat. No. 7,869,868.

(51) Int. Cl.
*A61N 1/39* (2006.01)
*A61N 1/375* (2006.01)

(52) U.S. Cl.
USPC ..................... 607/5; 607/2; 607/36

(58) Field of Classification Search
None
See application file for complete search history.

(56) References Cited

U.S. PATENT DOCUMENTS

| | | | |
|---|---|---|---|
| 4,094,321 | A | 6/1978 | Muto |
| D250,719 | S | 1/1979 | Jacobson et al. |
| D253,490 | S | 11/1979 | Reiser |
| D261,552 | S | 10/1981 | Boroda |
| D269,205 | S | 5/1983 | Langer et al. |
| D280,930 | S | 10/1985 | Speicher et al. |
| D318,539 | S | 7/1991 | Challard |
| D337,820 | S | 7/1993 | Hooper et al. |

(Continued)

FOREIGN PATENT DOCUMENTS

EP    0670605    9/1995

OTHER PUBLICATIONS

(PCT/US2008/050579) PCT Notification of Transmittal of the International Search Report and the Written Opinion of the International Searching Authority, Mailed Oct. 23, 2008, 10 pages.

*Primary Examiner* — Kennedy Schaetzle
(74) *Attorney, Agent, or Firm* — Reed A. Duthler (57) ABSTRACT

Capacitor packaging according to the disclosure provides advantages particularly in connection to compact and/or complex-shaped medical devices (e.g., having limited interior volume defined by domed and/or irregular exterior surfaces). In addition, capacitors of the type shown and described herein can be utilized in relatively compact external defibrillators, such as automatic external defibrillators or clinician-grade, automated or manually-operated external defibrillators. In one form a plurality of capacitors having substantially flat exterior surfaces are placed in an abutting relationship between at least a pair of major surfaces and the major surfaces are spaced from an opposing or adjacent surface in a non-parallel configuration. In other forms, one or more exterior surface portions have a common and/or complex radius dimension (i.e., the surfaces are curved).

14 Claims, 8 Drawing Sheets

(56) References Cited

U.S. PATENT DOCUMENTS

| | | |
|---|---|---|
| D343,901 S | 2/1994 | Anderson |
| 6,006,133 A | 12/1999 | Lessar |
| D418,919 S | 1/2000 | Sanders et al. |
| D478,990 S | 8/2003 | Kroll |
| 7,869,868 B2 * | 1/2011 | Swanson et al. .................. 607/5 |
| 2003/0204216 A1 | 10/2003 | Ries |
| 2004/0134874 A1 | 7/2004 | Hossick-Schott et al. |
| 2005/0154423 A1 | 7/2005 | Goedeke |
| 2006/0249774 A1 | 11/2006 | Sherwood |

* cited by examiner

DIVERSE CAPACITOR PACKAGING FOR MAXIMIZING VOLUMETRIC EFFICIENCY FOR MEDICAL DEVICES

RELATED APPLICATION

This application is a continuation of U.S. patent application Ser. No. 11/622,245, filed Jan. 11, 2007 now U.S. Pat. No. 7,869,868 entitled "DIVERSE CAPACITOR PACKAGING FOR MAXIMIZING VOLUMETRIC EFFICIENCY FOR MEDICAL DEVICES", herein incorporated by reference in its entirety.

CROSS REFERENCE TO RELATED APPLICATIONS AND PATENTS

This patent disclosure relates to and incorporates the entire contents of the following disclosures; namely, U.S. Pat. No. D523,144 entitled, "IMPLANTABLE MEDICAL DEVICE," U.S. Pat. No. 7,002,790 entitled, "CAPACITOR IN AN IMPLANTABLE MEDICAL DEVICE," U.S. Pat. No. 6,819,544 entitled, "DUAL-ANODE ELECTROLYTIC CAPACITOR FOR USE IN AN IMPLANTABLE MEDICAL DEVICE," U.S. Pat. No. 6,807,048 entitled, "ELECTROLYTIC CAPACITOR FOR USE IN AN IMPLANTABLE MEDICAL DEVICE," U.S. Pat. No. 6,802,951 entitled, "METHODS OF ANODIZING VALVE METAL ANODES," U.S. Pat. No. 6,855,456 entitled, "TITANIUM ALLOY-PIN BATTERY FEEDTHROUGH FOR AN IMPLANTABLE MEDICAL DEVICE," U.S. Pat. No. 6,819,544 entitled, "DUAL-ANODE ELECTROLYTIC CAPACITOR FOR USE IN AN IMPLANTABLE MEDICAL DEVICE," published U.S. patent application Ser. No. 11/348,681 entitled, "COMPLEX-SHAPED CERAMIC CAPACITORS FOR IMPLANTABLE MEDICAL CARDIOVERTER DEFIBRILLATORS AND METHOD OF MANUFACTURE" U.S. Pat. No. 7,570,996 which issued Aug. 4, 2009, and published application Ser. No. 10/692,649 entitled, "ADVANCED VALVE METAL ANODES WITH COMPLEX INTERIOR AND SURFACE FEATURES AND METHODS FOR PROCESSING SAME" U.S. Pat. No. 7,342,774 which issued Mar. 11, 2008.

FIELD OF THE INVENTION

The present invention relates to high efficiency packing for multiple electrical capacitors operatively coupled to circuitry within a medical device such as an implantable medical device (IMD) like an implantable cardioverter-defibrillator (ICD) or an extra-cardiac implantable defibrillator (EID).

SUMMARY

Capacitor packaging according to the invention provides advantages particularly in connection to compact and/or complex-shaped IMDs (e.g., having limited interior volume defined by domed and/or irregular exterior surfaces). In addition, the present invention can be utilized in relatively compact external defibrillators, such as automatic external defibrillators or clinician-grade, automated or manually-operated external defibrillators. Further uses include compact packaging for extra-cardiac implantable defibrillator (EID) which is typically implanted subcutaneously or sub-muscularly and the defibrillation electrodes are spaced from the heart (e.g., disposed in a non-transvenous location) and define a therapy vector that includes a reasonably large volume of myocardial tissue.

In one form of the invention a plurality of capacitors having substantially flat exterior surfaces are placed in an abutting relationship between at least a pair of major surfaces and the major surfaces are spaced from an opposing or adjacent surface in a non-parallel configuration.

In other forms of the invention, one or more exterior surface portions of the capacitors have a common and/or complex radius dimension (i.e., the surfaces are curved) that provides cooperating surfaces when coupled together. An additional aspect of the capacitors according to the invention relates to a common mass termination. That is, some embodiments of the invention include a single termination for the electrical connectors of the plurality of capacitors. In one embodiment an electronic module assembly (EMA) connector electrically and mechanically couples two or more discrete capacitors together. Such an EMA connector can couple to the capacitors at the center, or narrow end, of a set of pie-shaped capacitors. The EMA connector provides a convenient and reliable electrical connection from the capacitors to operative circuitry within a medical device. The EMA connector can be fabricated from a resin-based material which is over-molded over conductive wires or cables which are pre-configured to optimize assembly of the capacitor set. The over-molding can be performed in a single step or multiple steps. Injection molding and/or insert molding of the EMA connector conductors are two exemplary fabrication techniques according to the invention.

A wide variety of capacitors can be utilized according to the invention, including wet- or dry-electrolyte valve metal capacitors comprised of one or more pressed and sintered anodes disposed adjacent one or more cathode materials. Other types of capacitors include flat electrolytic capacitors such as those having a plurality of oxidized aluminum sheets interleaved together with alternating anode and cathode layers. The enclosure surrounding the anode(s) and cathode(s) can be conductive, non-conductive, metallic, coated, resin- or polymer-based, flexible or resilient, among other material packaging options.

Other options for practicing the invention include forms wherein the enclosure is case-positive, case-negative, or case-neutral. The polarity of the case can be maintained with use of insulated, hermetic feedthrough pins or other conductors (e.g., multi-layer co-fired ceramic feedthrough structures having conductive-paste electrical paths) as is known in the art. The capacitors can be electrically insulated from each other using selective deposition of dielectric material and/or intermediate insulative materials or they can be electrically coupled together (e.g., soldered, welded, or otherwise electrically joined).

Depending on the application, diverse non-prismatic capacitor enclosures can be used according to the invention. Such enclosures can be formed in a wide variety of ways including without limitation, mechanical drawing (e.g., so-called shallow or deep drawing of metallic sheets so that a single open side is adapted to receive the active capacitor components), plug molding, injection molding, stamping, punching, milling and the like. So-called clam shell enclosures can be employed without departing from the teaching of the present invention. Metallic enclosures can be laser welded, soldered, or otherwise conventionally coupled to ensure hermeticity.

Other aspects of the invention relate to methods and fixtures for fabricating components and enclosures for capacitors. For example, a pie-slice-shaped capacitor or set of capacitors can be fabricated having a non-, fully- or partially-rounded outer peripheral surface and flat, convergent side surfaces. Such capacitors can be readily fabricated using powered metal (e.g., valve metal, such as tantalum, titanium, niobium, zirconium, aluminum, and the like) and customized molds and press equipment.

According to this aspect of the invention, a unitary multi-part or split lower die can be utilized that defines a majority of the desired pie-slice-shape that cooperates with an upper portion of the split die that defines the convergent side surfaces. The lower portion of the split die is supported in a closed configuration and an optional powder-retaining sleeve coupled to an open upper portion of the lower split die. A lead wire can be placed partially within the die or it can be inserted into the powder during the powder filling process. That is, the lower split die is then partially filled (or filled or slightly over-filled) with the powered valve metal which is directed through the powder-retaining sleeve. As is known in the art one or more powder-binding substances can be added to or mixed into the powder prior to filling the die with the powder (and these substances are typically completely consumed during a subsequent sintering step).

Once the entire die is filled with powder the upper portion of the split die is directed through the sleeve and pressed into engagement with the powder thereby compressing the powder into the desired pie-slice-shape. The die components are then removed and the now pressed metal can be sintered into a porous member having karst-like structures before performing a forming procedure designed to produce a layer of oxide of predetermined depth (and, thus a desired predetermined operating voltage) as is known in the art.

In terms of the predetermined operating voltages for cardiac defibrillators, a wide range of energy levels can be utilized depending on the location of the electrodes used to deliver the defibrillation therapy. For example, for cardioversion therapy delivery a lower level energy is typically applied and for surface-based electrodes much higher levels of energy are delivered. While not intending to limit the present invention, the capacitor assemblies of the invention can typically range from about ten Joules (J) to over 150 J. The higher energy assemblies can be achieved by coupling several discrete capacitors together in series.

Along the same lines as the foregoing, cooperating or interlocking capacitors can be fabricated that together define diverse non-prismatic shapes including an elongated quarter- or half-cylinder, for example, having one substantially flat end surface and one continuously rounded end surface.

BRIEF DESCRIPTION OF THE DRAWINGS

FIGS. 4A through 4D illustrate several variations of embodiments of exemplary capacitor assemblies according to the invention, wherein FIGS. 4A, 4B, and 4D depict three discrete capacitors coupled together and FIG. 4C depicts a pair of discrete capacitors coupled together.

FIGS. 5A through 5E illustrate two views, plan and elevational, of several variations of embodiments of exemplary capacitor assemblies according to the invention, wherein FIGS. 5A and 5B depict three discrete capacitors coupled together and FIG. 5C depicts a pair of discrete capacitors coupled together while FIG. 5D depicts a nominal number (n) discrete capacitors.

DETAILED DESCRIPTION OF THE ILLUSTRATED EMBODIMENTS

In the following detailed description, references are made to illustrative embodiments for compact capacitors for use in providing energy for medical devices including external and implantable medical devices (IMDs) such as implantable cardioverter-defibrillators (ICDs).

The present invention provides enhanced volumetric efficiency so that the overall size of an IMD is reduced as much as practicable.

In accordance with an aspect of the present invention, methods and apparatus are provided for fabricating capacitors and for enclosing said capacitors within an IMD.

Figure 1A:
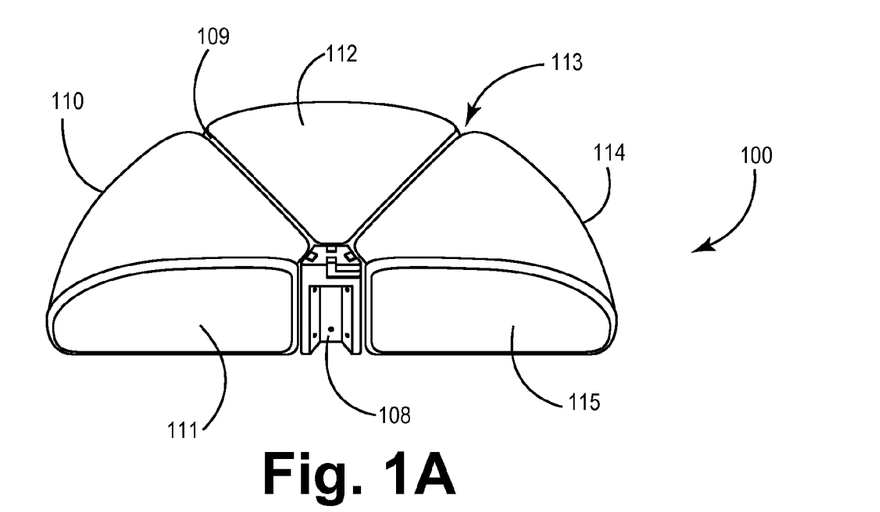
FIGS. 1A and 1B are perspective views of an embodiment of an exemplary capacitor assembly according to the invention.
Figure 1B:
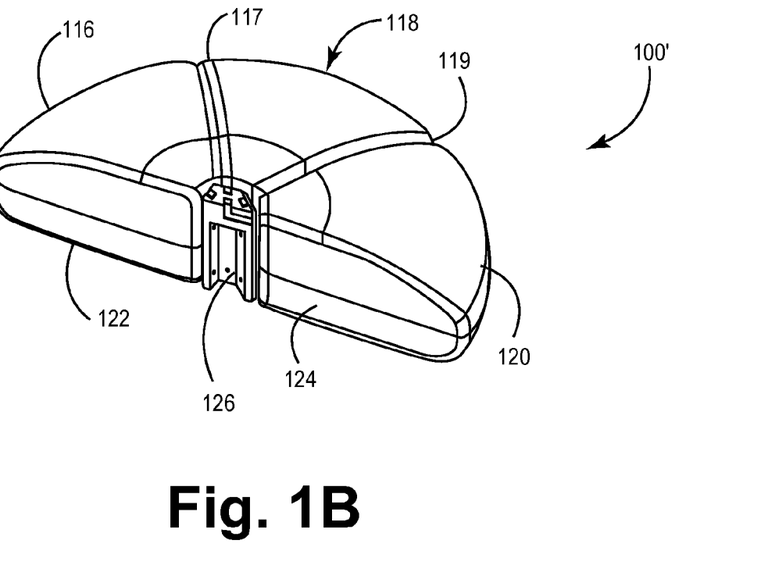

FIGS. 1A and 1B are perspective views of an embodiment of an exemplary capacitor assembly 100,100' according to the invention wherein three discrete capacitors 110,112,114 and 116,118,120, respectively, have a common truncated pie-slice shape in plan view. The three capacitors depicted in FIGS. 1A and 1B are exemplary but a greater or lesser number of capacitors can be employed. In cross section each capacitor is characterized by a substantially planar base surface (not shown) opposing a substantially curving upper surface and separated by substantially planar side surfaces (surfaces 111 and 115 and surfaces at interfaces 109,113 in FIG. 1A and surfaces 122 and 124 and surfaces at interfaces 117, 119 in FIG. 1B). The narrow ends of the capacitors are slightly truncated to accommodate a mass electrical termination unit 108,126. The unit 108,126 also functions to physically couple the capacitors together. The wide end of the capacitors is generally curved in plan view and progressively thinner in a height dimension than the narrow end of the capacitors.

Figure 2A:
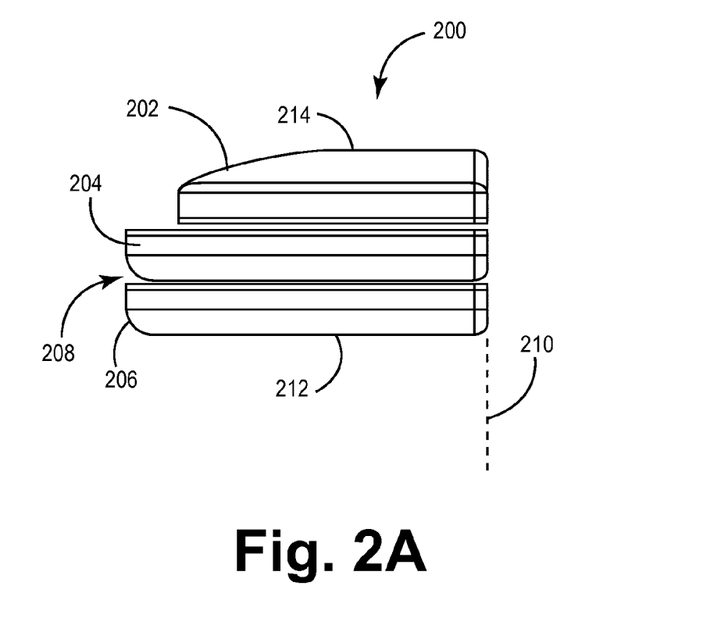
FIGS. 2A and 2B depict a side elevational view and a perspective view, respectively, of an embodiment of another exemplary capacitor assembly according to the invention.
Figure 2B:
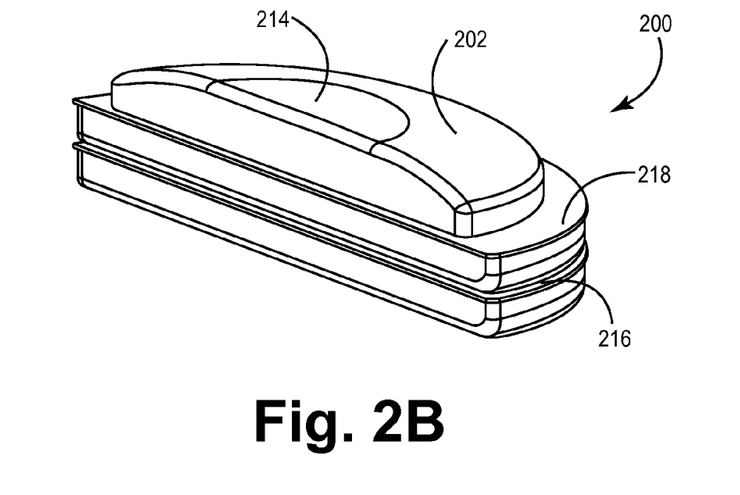

FIGS. 2A and 2B depict a side elevational view and a perspective view, respectively, of an embodiment of another exemplary capacitor assembly 200 according to the invention. Referring now to FIG. 2A, three D-shaped (or half-pie shaped) capacitors 202,204,206 stack together such that a common lateral termination (at 210) opposes an opposing stepped alignment. That is, capacitors 204,206 are substantially identical and have abutting surfaces (at 208), but capacitor 204 is slightly larger in radius that capacitor 202.

Thus, the substantially planar major lower surface 212 of capacitor 206 opposes the substantially flat peninsula portion 214 of dome-shaped major upper surface of capacitor 202. As can be seen with reference to FIG. 2B the step 218 is of an arbitrary size but can be reduced to mimic the nominal size of abutting peripheral surface 216 (e.g., capacitor 202 can have a larger radius or area similar to that of capacitor 204). Note that although capacitor 202 is depicted as a unitary capacitor, the capacitor assembly depicted in FIGS. 1A and 1B (110, 112,114 and 116,118,120) can be substituted in lieu of the unitary capacitor 202. It should be noted that the individual capacitors may have the same or different volumes, and the same or different capacitance values. Recognizing that there should be sufficient cathode capacitance to prevent excessive voltage reversal. Also, this embodiment may result in different anode to cathode capacitance ratios for the different capacitors.

Figure 3:
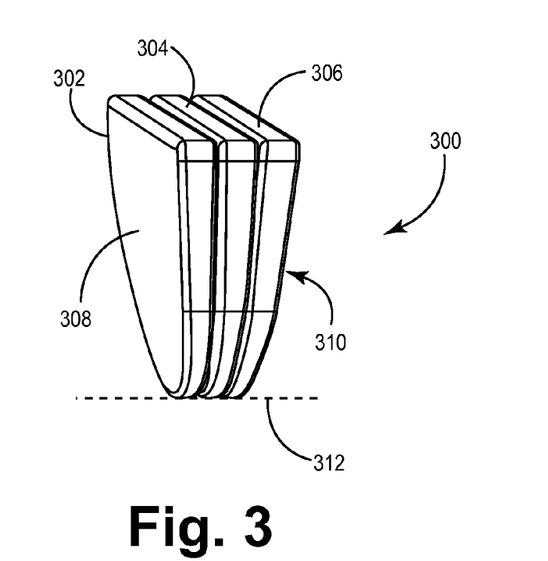
FIG. 3 is a perspective view of yet another embodiment of an exemplary capacitor assembly according to the invention.

FIG. 3 is a perspective view of yet another embodiment of an exemplary capacitor assembly 300 according to the invention. As illustrated in FIG. 3 three discrete D-shaped capacitors 302,304,306 are arranged in a stack aligned at a common edge (shown by dashed line 312) and having non-parallel opposing major surfaces 308,310 on the end capacitors 302, 306. The thickness dimension of each capacitor is relatively reduced at aligned common edge (312) than at the opposing substantially flat side. The dimensions provide for an overall capacitor assembly 300 that is compact and readily adaptable to be disposed in a lower portion of a letter-D-, tear-drop- or curved-shaped IMD that has non-parallel opposing major surfaces.

Figure 4:
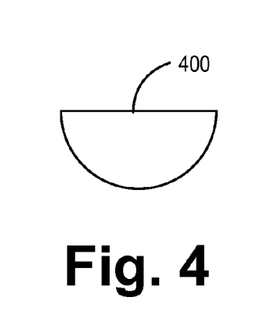
FIG. 4 is a plan view of a deception of D-shaped capacitors.
Figure 4A:
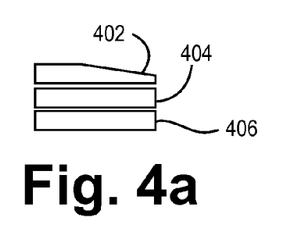
Figure 4B:
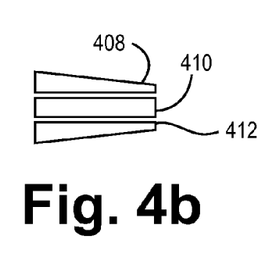
Figure 4C:
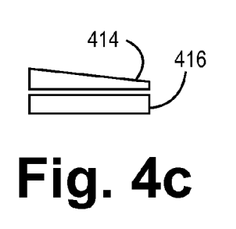
Figure 4D:
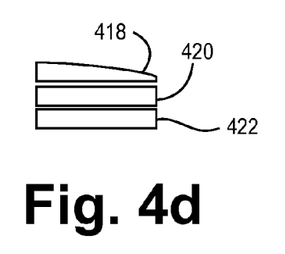

FIGS. 4A through 4D illustrate several variations of embodiments of exemplary capacitor assemblies according to the invention and similar to the assembly 300 of FIG. 3 (having a D-shaped configuration when viewed in plan). Wherein FIGS. 4A, 4B, and 4D depict three discrete capacitors coupled together (402,404,406; 408,410,412; 418,420, 422 respectively) and FIG. 4C depicts a pair of discrete capacitors 414,416 coupled together.

Although a D-shaped plan view of capacitors 400 is depicted in FIG. 4, the capacitors 400 can be any arbitrary configuration. As can be appreciated a wide variety of combinations of capacitors can be employed with respect to the cross-sectional dimensions. As depicted in FIG. 4A the two capacitors 404,406 are the same size and both have a constant thickness dimension. In contrast to capacitor 402 which has a common area but differs in thickness from a first edge to an opposing second edge. Referring now to FIG. 4B the capacitors 408,410,412 each resemble the capacitors depicted in FIG. 3, although arguably with a slightly more pronounced variation in thickness from a first to an opposing second edge. In FIG. 4D, like FIG. 4A, the two lower capacitors 420,422 are substantially the same size, shape and thickness, but the upper capacitor 418 has a curved upper surface from a very thin first edge to a relatively thick opposing second edge. Referring to FIG. 4C a lower capacitor 416 has consistent thickness and upper capacitor 412 has a varying thickness dimension from a first side to an opposing second side. As a result of the combinations of capacitors depicted in FIG. 4A-4D a series of compact capacitor assemblies are provided that minimize volume within a curving and/or domed portion of an IMD.

Figure 5:
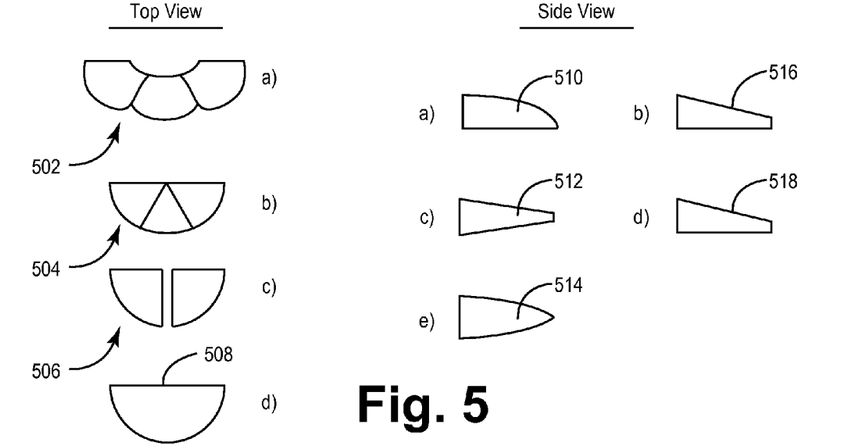

FIG. 5 illustrate two views, a series of plan views of capacitor assemblies 502,504,506 and elevational views of elevational side views of discrete cross sections of individual capacitors 510,512,514,516,518. Several variations of embodiments of exemplary capacitor assemblies can thus be realized using these diverse configurations according to the invention, including assemblies comprised of three discrete capacitors coupled together (502,504), a pair of discrete capacitors coupled together (506), and a stacked assembly of a nominal number (n) discrete capacitors (508). The assemblies 502,504,506,508 depicted in FIG. 5 can be fabricated from a series or stack of one or more of the capacitors 510, 512,514,516,518 depicted in cross-section in FIG. 5. Unlike the assembly depicted in FIGS. 1A and 1B, no mass electrical termination or conductive feedthrough is depicted in FIG. 5 although those of skill in the art can appreciate diverse components and arrangement to electrically couple the capacitors.

Figures 6A, 6B:
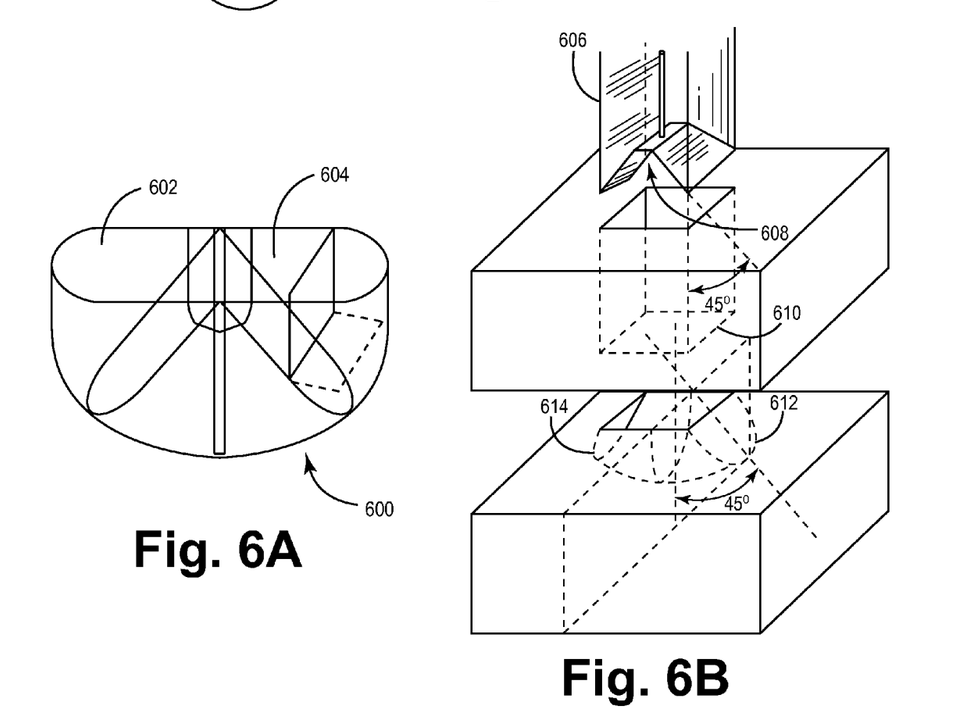
FIGS. 6A and 6B depict a perspective view (partially in ghost) of a pie-shaped capacitor disposed within a curbed housing for an implantable medical device (IMD) and an exploded view of discrete fixtures configured to press powdered metal into a desired shape for a capacitor according to the invention, respectively.

FIGS. 6A and 6B depict a perspective view (partially in ghost) of a pie-shaped capacitor 604 disposed within a curved housing 602 for an implantable medical device (IMD) and an exploded view of discrete fixtures 606,608,610, 612,614 configured to press powdered metal (not shown) into a desired shape for a capacitor according to the invention, respectively. According to this aspect of the invention, a split lower die 612,614 is utilized that defines a majority of the desired pie-slice-shape that cooperates with an upper portion of the split die 608 that defines the convergent side surfaces of a valve metal anode. The lower portion of the split die 612,614 is supported on structure 616 in a closed configuration and an optional powder-retaining sleeve 610 coupled to an open upper portion of the lower split die 612,614. A lead wire (not shown) can be placed partially within the die 608, 612,614 or it can be inserted into the powder during the powder filling process. Then the lower split die 612,614 is then partially filled (or filled or slightly over-filled) with a powered valve metal which is directed through the powder-retaining sleeve 610. As is known in the art one or more powder-binding substances can be added to or mixed into the powder prior to filling the die with the powder (and these substances are typically completely consumed during a subsequent sintering step).

Figure 7:
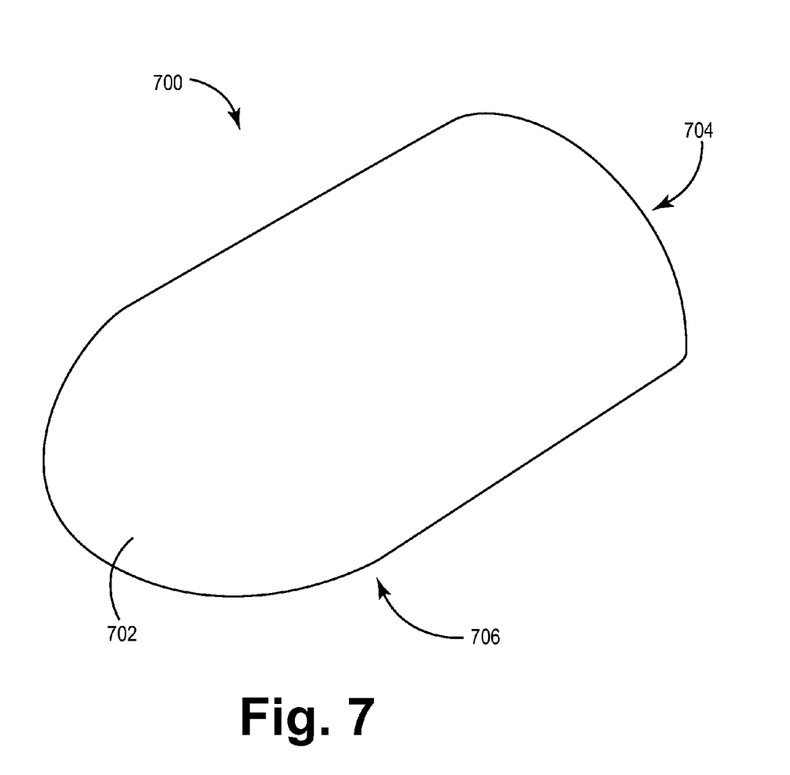
FIG. 7 is a perspective view of a unitary capacitor shaped like a quarter-cylinder with a first end substantially orthogonal to its longitudinal axis and a continuously curved end opposing said first end.

FIG. 7 is a perspective view of a unitary capacitor 700 shaped like a half-cylinder with a first end 704 substantially orthogonal to its longitudinal axis and a continuously curved end 702 opposing said first end 704. The capacitor 700 can be pressed as described and depicted in conjunction with FIG. 6 and adapted to be received in a portion of an IMD having a similar curving outer surface. The capacitor 700 can be disposed adjacent a curved outer surface and a substantially flat portion of an IMD adjacent a prismatic battery or hybrid electronic board or boards (not shown) or the like.

Figure 8:
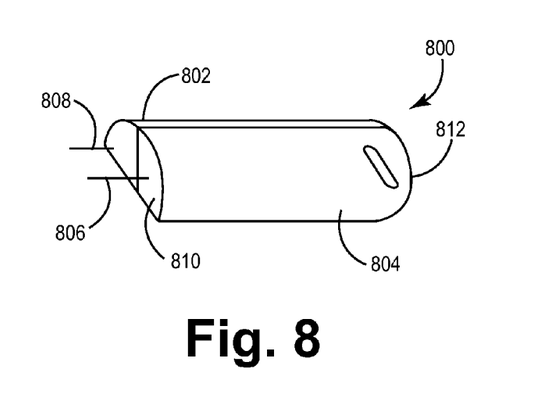
FIG. 8 is a perspective view of a pair of capacitors which together defined a shape like the quarter cylinder depicted in FIG. 7.

FIG. 8 is a perspective view of a pair of quarter-cylinder capacitors 802,804 which together defined a shape like the half-cylinder capacitor 700 depicted in FIG. 7. In FIG. 8, each capacitor 802,804 closely resembles the other capacitor by having a curved end 812 opposing a flat surface 810 orthogonal the longitudinal axis of the capacitor. In addition, each capacitor 802,804 includes a conductive pin 806,808 which couples to one of an anode or a cathode disposed within the capacitor. While two capacitors are depicted in FIG. 8, three or more capacitors can be employed. Furthermore, the capacitors do not have to have the same dimensions (i.e., outer circumference) but could for example comprise a quarter-cylinder and two one-eighth cylinder capacitors.

Figure 9:
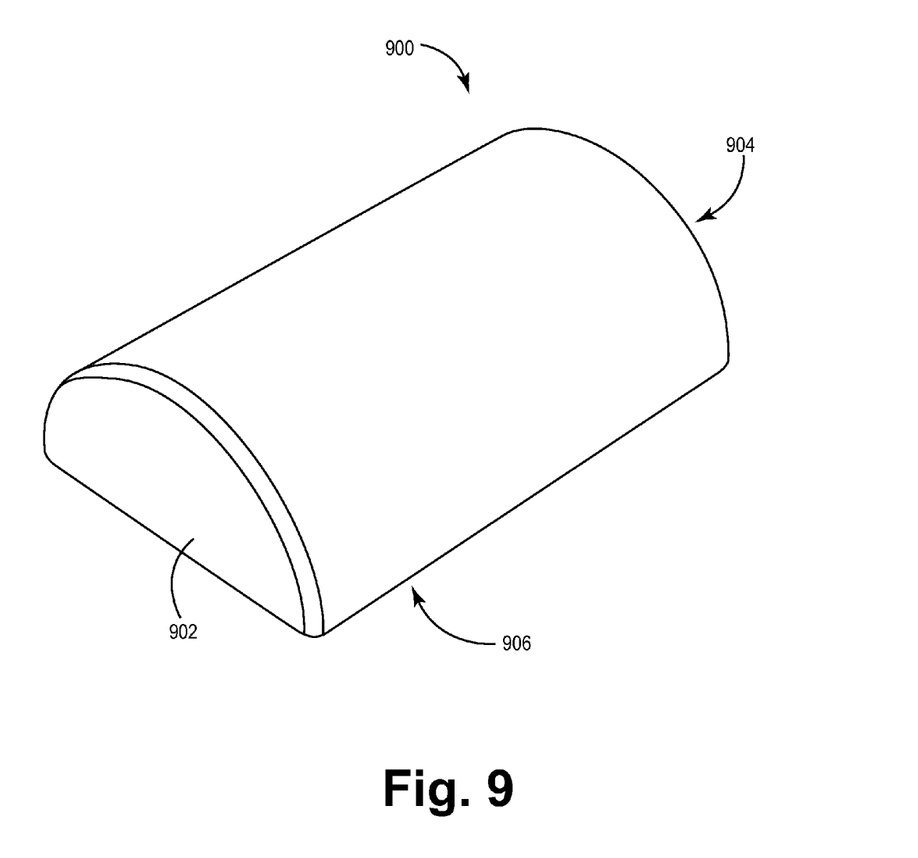
FIG. 9 is a perspective view of a unitary capacitor shaped like a half-cylinder.

FIG. 9 is a perspective view of a unitary capacitor 900 shaped like a half-cylinder having opposing ends 902,904 disposed substantially parallel from each other and separated by a continuously curving major surface coupled to a substantially planar surface (not shown).

Figure 10:
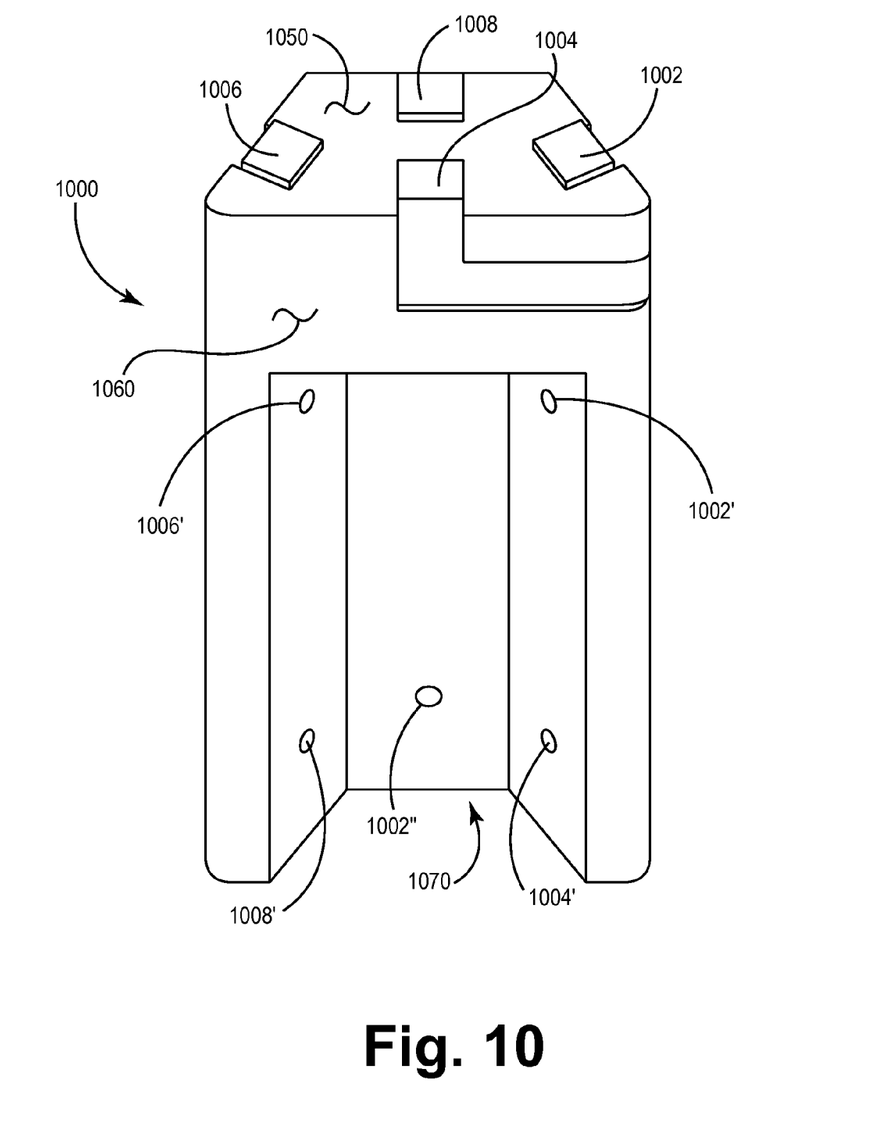
FIG. 10 is a perspective view of an exemplary EMA connector according to certain aspects of the invention which includes discrete elongated conductors mechanically coupled to individual side walls of the body of the EMA connector that each electrically couple to an anode and a cathode of a capacitor for a capacitor assembly of at least two discrete capacitors.

FIG. 10 is a perspective view of an exemplary EMA connector 1000 according to certain aspects of the invention which includes discrete elongated conductors 1002,1004,1006,1008 mechanically coupled to individual side walls of the body of the EMA connector 100 that each electrically couple to at least one anode and cathode (not shown) of each capacitor for a capacitor assembly comprising at least two discrete capacitors. The side walls of the embodiment depicted in FIG. 10 is configured for three pie-shaped capacitors as elsewhere depicted herein although diverse sizes and shapes can be utilized with EMA connectors modified from that shown in FIG. 10. Mechanical coupling of each capacitor can be achieved by inserting protruding conductive pins (not shown) through aperture(s) formed in one or more of the conductors 1002,1004,1006,1008. The apertures are denoted in FIG. 10 by prime and double prime notations (' and "). As will be appreciated with reference to FIG. 11, the pins can be mechanically fixated on the reverse side of the apertures (e.g., welded, soldered, capped, mechanically deformed, etc.). Depending on the desired electrical configuration (electrically coupled in series or in parallel) the conductors can be serpentine in order to make connection to more than one capacitor. In FIG. 10, conductors 1002,1008 couple at least one pin of more than one capacitor (at 1002',1002" and 1008'). All of the conductors commonly terminate at surface 1050. In the event that the conductors are disposed in a recess or channel along all or part of their length, the portions terminating at surface 1050 are exposed above, below, or substantially coplanar with said surface. Thus, additional electrical connections can more readily be achieved. For instance a wire bonding technique or a mating portion of a structure complementary to the EMA connector 1000 can be utilized to couple the conductors to remote components and/or circuitry (not shown).

Figure 11:
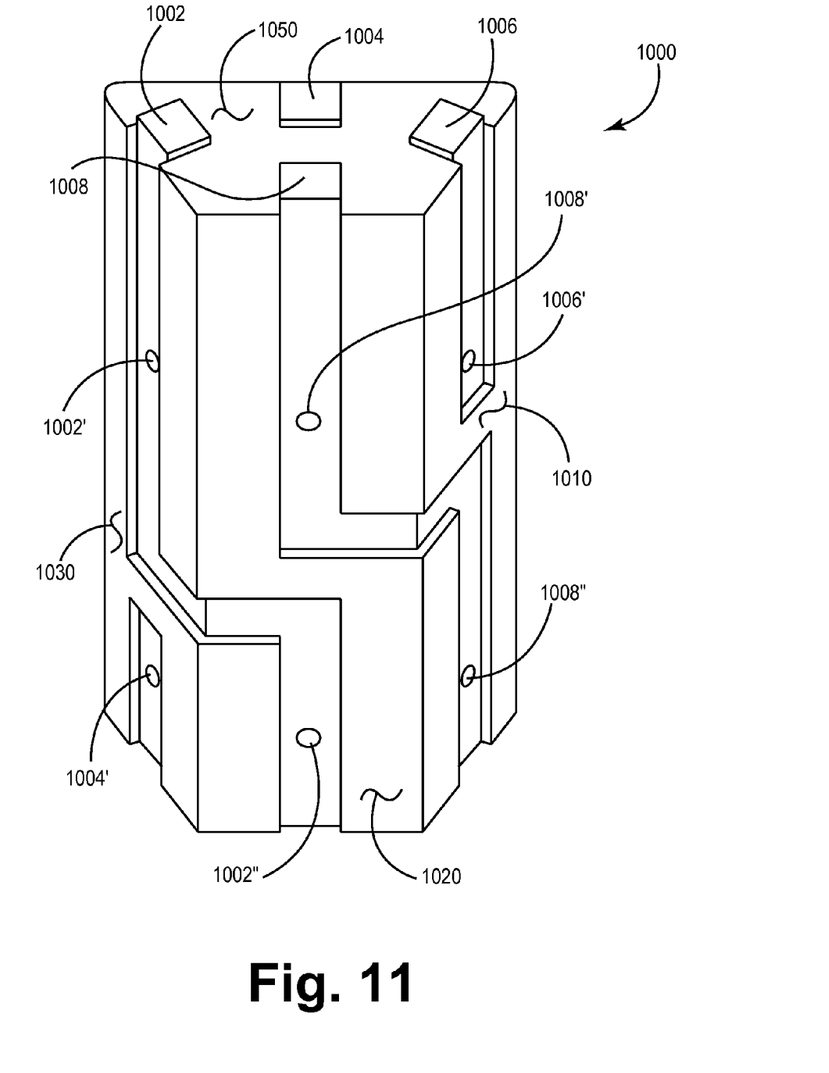
FIG. 11 is a perspective view of a reverse side of an EMA connector as illustrated in FIG. 10 in which the dual conductors for each capacitor is clearly depicted for an embodiment of a capacitor assembly according to the present invention.

FIG. 11 is a perspective view of a reverse side of an EMA connector 1000 as illustrated in FIG. 10 in which the dual conductors for each capacitor is clearly depicted for an embodiment of a capacitor assembly according to the present invention. With respect to the apertures (denoted by prime and double-prime notations—' and "—respectively) in an alternate form of the invention these apertures are used in an insert molding operation and they are used to admit a boss or peg thereby further mechanically coupling the conductors to the EMA connector 1000. When assembled with discrete capacitors the electrical connections can be wire bonded, welded, and/or soldered together with electrical lead wires from the capacitors.

If we assume that all of the capacitors are the same, then each one will have a feedthrough pin and a stud pin welded to the encasement. The electrical connection of the capacitors requires a connection to the feedthrough pin only of one capacitor; conductor 1006 serves this purpose. The stud pin of that capacitor is then connected in series with the feedthrough pin of capacitor 2; conductor 1008 serves that purpose. The stud pin of capacitor is then connected in series with the feedthrough pin of an adjacent capacitor; conductor 1002 serves that purpose. What remains is a connection to the encasement only of the final adjacent capacitor. For this particular connector design concept, the method of electrical connection to the encasement of capacitor would be used for a jumper wire to connect the case and conductor labeled as 1004 in FIG. 10. The stud pin on each capacitor (since all capacitors are the same, they would all have conductive stud pins) needs to be accommodated in the connector design. The hole in the connector labeled 1004' in FIG. 10 and corresponding geometry on the opposite side in FIG. 11 provides this accommodation of the stud pin. In addition, the connector is designed so that this stud pin can be welded to the connector, thus providing mechanical (structural) stability to the capacitors in the assembly.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. An assembly of capacitors adapted to be disposed within an implantable medical device, comprising:
at least a pair of individually-packaged electrical capacitors wherein said at least a pair of capacitors comprises: first and second capacitors, said first and second capacitors having non-parallel, substantially flat opposing major side surfaces and cooperatively coupled together to define a capacitor assembly, and wherein one of the major side surfaces of the first capacitor is located facing one of the major side surfaces of the second capacitor; and
at least one of: an electronic module assembly (EMA) connector, a flexible circuit, and an elongated electrical conductor electrically and mechanically coupling said first capacitor and said second capacitor together.

2. A compact assembly of capacitors according to claim 1, wherein said first capacitor and said second capacitor comprise valve metal capacitors.

3. A compact assembly of capacitors according to claim 2, wherein said first capacitor and said second capacitor are fabricated from at least one of the group: a tantalum metal, a niobium metal, a titanium metal, an aluminum metal, a zirconium metal, an alloy comprised of at least one of the foregoing metals.

4. A compact assembly of capacitors according to claim 1, wherein said the opposing major side surfaces of the first capacitor are D-shaped.

5. A compact assembly of capacitors according to claim 4, wherein the first capacitor further comprises a substantially continuously radiused second surface coupling to both of the major opposing, non-parallel surfaces.

6. A compact assembly of capacitors according to claim 5 further comprising a substantially planar third surface coupling the second surface and the major opposing, non-parallel surfaces.

7. A compact assembly of capacitors according to claim 6, wherein the substantially continuously radiused second surface is configured into one of a partial ovoid, a D-shaped member, a C-shaped member.

8. A compact assembly of capacitors according to claim 7, wherein the substantially continuously radiused second surface includes an increased thickness proximate the third surface and a reduced thickness spaced from the third surface.

9. A compact assembly of capacitors according to claim 1, further comprising at least one additional capacitor and wherein the assembly comprises the first capacitor, the second capacitor, and the at least one additional capacitor.

10. A compact assembly of capacitors according to claim 1, further comprising an implantable medical device (IMD) containing the capacitor assembly.

11. A compact assembly of capacitors according to claim 10, wherein the IMD comprises one of an implantable cardioverter-defibrillator (ICD) and an extra-cardiac implantable defibrillator (EID).

12. A compact assembly of capacitors according to claim 10, wherein an interior surface of said implantable medical device comprises a partially curved domed interior surface opposing a substantially flat interior surface.

13. A compact assembly of capacitors according to claim 1, wherein the assembly comprises a set of pie-shaped capacitors.

14. A compact assembly of capacitors according to claim 1, wherein the assembly comprises a non-prismatic capacitor assembly.

* * * * *